(12) United States Patent
Baruschke et al.

(10) Patent No.: US 6,315,561 B1
(45) Date of Patent: Nov. 13, 2001

(54) TOOTH ROOT IMPLANT

(75) Inventors: Michael Baruschke, Berlin; Helmut Käufer, Mettmann; Alexander Bongers, St. Wendel, all of (DE)

(73) Assignees: Alfred Ransmayer; Albert Rodrian

( * ) Notice: Subject to any disclaimer, the term of this patent is extended or adjusted under 35 U.S.C. 154(b) by 0 days.

(21) Appl. No.: 09/341,608

(22) PCT Filed: Feb. 4, 1998

(86) PCT No.: PCT/DE98/00395

§ 371 Date: Jul. 14, 1999

§ 102(e) Date: Jul. 14, 1999

(87) PCT Pub. No.: WO98/34560

PCT Pub. Date: Aug. 13, 1998

(30) Foreign Application Priority Data

Feb. 11, 1997 (DE) .............................................. 197 07 310

(51) Int. Cl.⁷ ...................................................... A61C 8/00
(52) U.S. Cl. ............................................................ 433/173
(58) Field of Search .................................. 433/173, 174, 433/175, 176, 201.1; 623/16

(56) References Cited

U.S. PATENT DOCUMENTS

| 2,721,387 | * | 10/1955 | Ashuckian ............................ 433/173 |
| 3,934,347 | | 1/1976 | Lash et al. . |
| 4,244,689 | | 1/1981 | Ashman . |
| 4,252,525 | | 2/1981 | Child . |
| 4,772,203 | * | 9/1988 | Scheunemann ........................ 433/173 |
| 4,812,120 | | 3/1989 | Flanagan et al. . |
| 5,344,457 | * | 9/1994 | Pilliar .................................... 433/174 |
| 5,639,237 | * | 6/1997 | Fontenot ................................ 433/173 |
| 5,820,374 | * | 10/1998 | Simmons et al. ..................... 433/173 |

FOREIGN PATENT DOCUMENTS 9513028   5/1995  (WO) .

* cited by examiner

Primary Examiner—Todd E. Manahan
(74) Attorney, Agent, or Firm—Mark P. Stone

(57) ABSTRACT

An implant has a base body (9) with a fiber-threaded outer surface (2) for promoting in-growth in a jaw bone. The fibers (5) extracted from the base body (9) have a rugged structure to facilitate the settlement of human tissue cells on the base body (9).

20 Claims, 2 Drawing Sheets

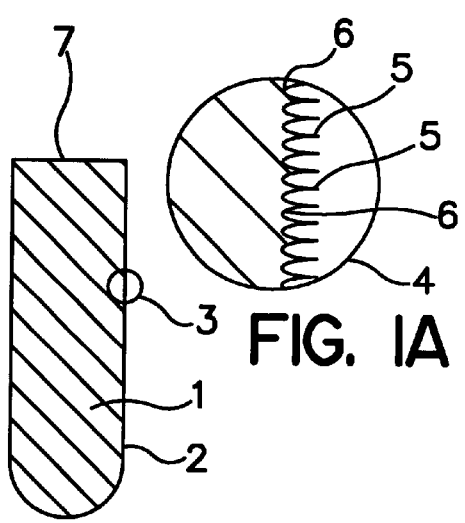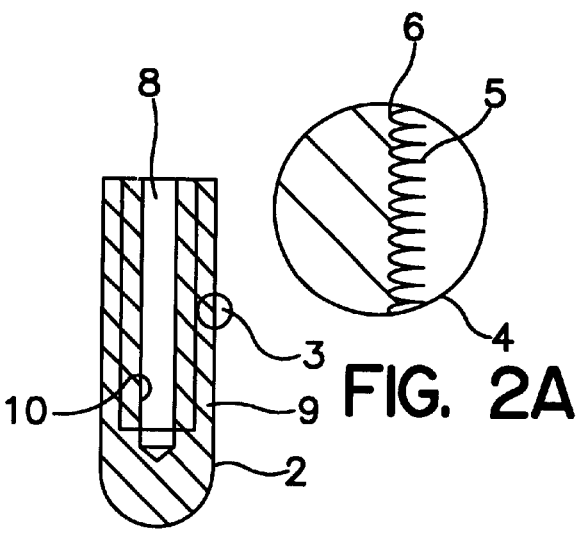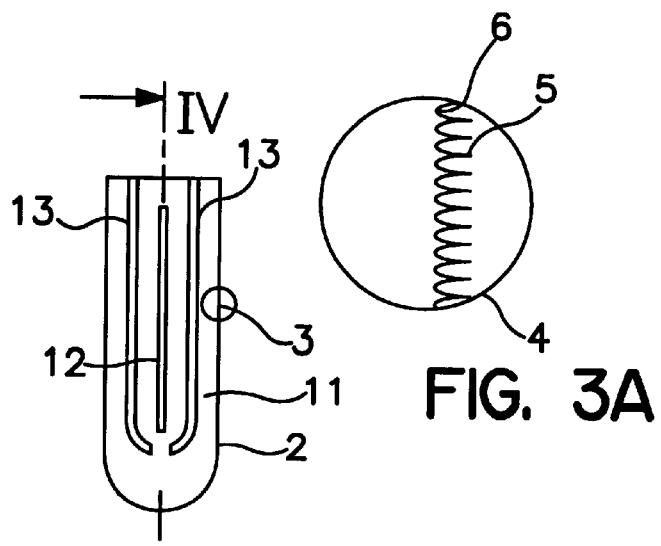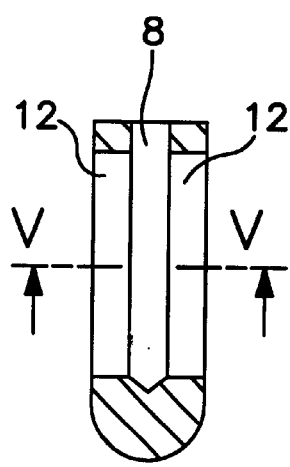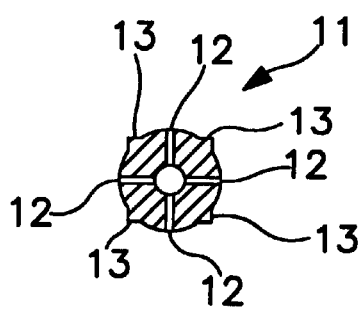

TOOTH ROOT IMPLANT

TECHNICAL FIELD

The invention relates to an implant, in particular a tooth root implant, with a main body which is designed as an elastic body made of plastic.

PRIOR ART

As Fallschüssel has stated in "Zahnärztliche Implantologie" [Dental Implantology], Quintessenz Verlag GmbH, Berlin et al., 1986, pages 94–95, a large number of plastics are used in medicine for implantation purposes. It is also known, from U.S. Pat. No. 4,531,916, to provide tooth root implants made of different materials with a porous plastic shell in order to make it easier for body tissue to grow into the surface of the implant. In the dental sector, plastic implants afford the advantage of giving the patient a more normal "chewing feel" compared to metal implants. The reason for this is probably that the structure of plastics deviates from the structure of the jaw bone tissue to a lesser extent than does a metal structure. A problem which arises particularly often in the case of metal implants, but which has not as yet been satisfactorily remedied in plastic implants either, is that the ingrowth times for the implants are relatively long. Particularly in the case of metal implants, ingrowth times of up to six months are not unusual.

The U.S. Pat. No. 3,934,347 already suggested, in order to improve the ingrowth of an implant, to surround a metal cylinder which comprises a flange and at one end a bottom, with a silicone-embedded ceramic or metal ring and to attach fibrous matting or woven material to certain portions of the silicone rubber with the fibres being embedded into or glued onto the silicone rubber. The known implant is not only complicated as far as its construction is concerned but also consumes relatively much space which, as a result, weakens the jawbone.

DESCRIPTION OF THE INVENTION

The object on which the invention is based is that of making available an implant which, specifically when used in the dental sector, significantly reduces the ingrowth times and additionally ensures better homogeneity of implant and implant-retention site. According to the invention, this object is achieved, in an implant of the type set out in the introduction, by the fact that at least part of the outer surface of the main body is fibred, that the fibres of the fibred outer surface have, in the area near the main body, in each case a transition zone with a cross-section widening towards the main body, and that the strength of the plastic in the area of the fibres is greater than in the remainder of the main body.

The implant according to the invention affords the advantage that the fibre-structured outer surface of the implant connects to the body tissue in, as it were, a tentacle-like manner. This not only appreciably shortens the ingrowth times; it also gives a transition zone, between plastic implant and body tissue, which performs a buffer function, both in the event of sudden loads impacting on the implant and also in the normal process of mastication.

It is particularly advantageous if the main body of the implant is provided with a bore, and with slots which extend over part of the length of the main body and make it easier to widen the main body out. Widening the main body out by introducing suitably dimensioned screws into the bore of the main body makes it possible, in the dental sector, for the diameter of the main body, which has been widened out upon implantation, to be decreased more or less continuously during the ingrowth phase, and thus makes it possible to influence the size and the structure of the abovementioned buffer zone.

BRIEF DESCRIPTION OF THE DRAWINGS

FIG. 1 shows a tooth root implant designed as a solid body, and

FIG. 1A illustrates an enlarged view of a portion of FIG. 1,

FIG. 2 shows a tooth root implant designed as a hollow body with internal thread, and FIG. 2A illustrates an enlarged portion of FIG. 2, FIG. 3 shows a tooth root implant designed as a hollow body with longitudinal slots, and FIG. 3A illustrates an enlarged view of a portion of FIG. 3, FIG. 4 shows a section along the line IV—IV in FIG. 3, FIG. 5 shows a section along the line V—V in FIG. 4.

MEANS OF IMPLEMENTING THE INVENTION

Figure 6:
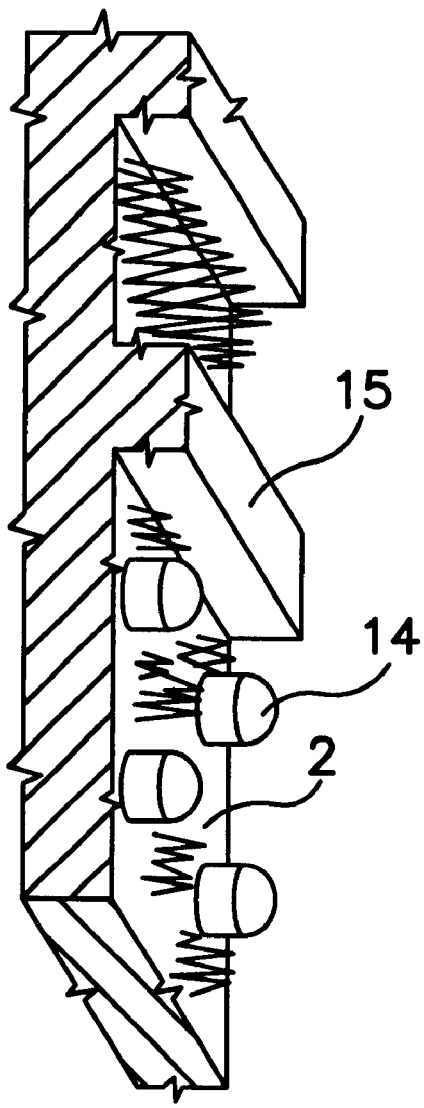
FIG. 6 shows a surface cut-out of a modified implant.

In FIG. 1, reference 1 is the main body of a tooth root implant, made of a biocompatible plastic. The cylindrical outer surface 2 of the main body 1 is not smooth, and instead has a micro-structure which can be described as fibred, as is indicated on an enlarged scale in the circle 4 (FIG. 1A) corresponding to the cut-out 3 of the main body 1. This shows a multiplicity of fibres 5 which, in the area of their transition to the main body 1, have a zone 6 in which their cross-section increases towards the main body. The fibres 5 are, in other words, formed by tapering, irregular micro-projections of the outer surface 2 of the main body. While the greater part of the outer surface of the main body 1 is fibred, i.e. is provided with oriented micro-fibres and/or hollow micro-fibres of irregular shape and size, its end face 7 is left smooth. The smooth end face 7 can be used to connect a plastic component to the tooth root implant by hot-plate welding, the said plastic component being fused to the end face 7 by means of a rubbing movement.

FIGS. 2 and 2A show a main body 9 which is provided with a central bore 8 and whose cylindrical outer surface 2 is once again fibred, as in the case of the main body 1. The bore 8 is provided with an internal thread 10 for receiving screws (not shown). By choosing a suitable screw diameter, the implant can be inserted, in a slightly widened state, into the bore provided in the patient's jaw and intended to receive the implant.

In the case of the tooth root implant represented in FIGS. 3 and 3A to 5, the main body 11 has, in addition to a central bore 8, four slots 12 distributed about its circumference and making it easier to spread open, and four longitudinal ribs 13 used for centering it and securing it in terms of rotation.

In order to prevent the fibres 5 from being pressed flat during insertion into a receiving seat which has been previously prepared for this purpose in a patient's jaw bone, it may be expedient, as is represented in FIG. 6, to provide the cylindrical outer surface 2 of the respective main body additionally with nipple-shaped and/or ridge-shaped spacer elements 14 and 15, respectively. The interspaces between the spacer elements 14 and 15 can also be used for applying a coating of a substance which promotes bone growth, preferably in the form of collagens.

Figure 7:
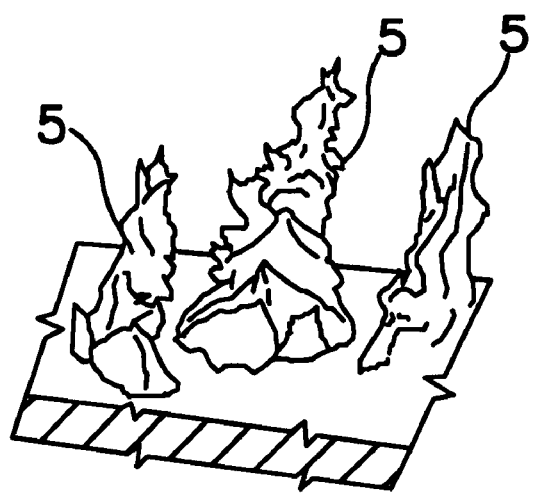
FIG. 7 shows, on a much enlarged scale, the fibres protruding from the outer surface of the main body of an implant.

Finally, FIG. 7 shows that the fibres 5 are not more or less smooth structures with a continuously tapering cross-section, but instead have a distinctly rugged structure with lamellar or lobular excrescences, which structure favours the attachment of body tissue cells. The fibres 5 can be of unequal lengths, the maximum length being 1 mm in the case of tooth implants. By changing the length and the micro-structure of the fibres 5, it is possible to adapt the implant to the structure of the bone which is intended to receive it.

By virtue of the fact that the fibres 5, in the course of the manufacture of the implants, are extracted from the respective main body by, in a manner of speaking, breaking open the outer surface thereof, and this results in a stretching of their molecular structures, a desired effect is obtained which is that there is an increase in the modulus of elasticity, which leads in particular to an increase in the tensile strength of the fibre material compared to the tensile strength of the plastic of the main body.

Implants with an essentially cylindrical main body are shown in the figures. However, when using so-called direct implants, the main body can instead also be given the shape of the respective tooth root which has been extracted.

What is claimed is:

1. A tooth root implant with a main body (1; 9; 11) which is designed as an elastic body made of plastic, characterized in that at least part of the outer surface (2) of the main body (1; 9; 11) is fibred, in that the fibres (5) of the fibred outer surface (2) have, in the area near the main body, in each case a transition zone (6) with a cross-section widening towards the main body (1; 9; 11), and in that the strength of the plastic in the area of the fibres (5) is greater than in the remainder of the main body (1; 9; 11).

2. Implant according to claim 1, characterized in that the main body (9; 11) is provided with a central bore (8).

3. Implant according to claim 2, characterized in that the main body (11) is provided with slots (12) extending over part of its length.

4. Implant according to claim 2, characterized in that the outer surface (2) of the main body is provided with spacer elements (14, 15) formed by projections of the main body.

5. Implant according to claim 2, characterized in that the outer surface (2) of the main body (11) is provided with longitudinal ribs (13).

6. Stand according to claim 2, characterized in that the fibers (5) are of unequal length.

7. Implant according to claim 2, chracterized in that the fibers (5) have a rugged surface structure.

8. Implant according to claim 1, characterized in that the main body (11) is provided with slots (12) extending over part of its length.

9. Implant according to claim 8, characterized in that the bore (8) is provided with an internal thread (10).

10. Implant according to claim 8, characterized in that the outer surface (2) of the main body is provided with spacer elements (14, 15) formed by projections of the main body.

11. Implant according to claim 2, characterized in that the bore (8) is provided with an internal thread (10).

12. Implant according to claim 11, characterized in that the outer surface (2) of the main body is provided with spacer elements (14, 15) formed by projections of the main body.

13. Implant according to claim 1, characterized in that the outer surface (2) of the main body is provided with spacer elements (14, 15) formed by projections of the main body.

14. Implant according to claim 13, characterized in that the spacer elements (14) are of nipple-shaped design.

15. Implant according to claim 13, characterized in that the spacer elements (15) are of ridge-shaped design.

16. Implant according to claim 1, characterized in that the outer surface (2) of the main body (11) is provided with longitudinal ribs (13).

17. Implant according to claim 1, characterized in that the fibres (5) are of unequal length.

18. Implant according to claim 1, characterized in that the fibres (5) have a rugged surface structure.

19. Implant according to claim 1, characterized in that the outer surface (2) of the main body (1; 9; 11) is provided with a coating which promotes bone growth.

20. Implant according to claim 1, characterized in that the main body has a contour adapted to the shape of an extracted tooth root.

* * * * *